United States Patent [19]

Yoon

[11] 4,374,523
[45] * Feb. 22, 1983

[54] OCCLUSION RING APPLICATOR

[76] Inventor: In B. Yoon, 2213 Forest Ridge Rd., Timonium, Md. 21093

[*] Notice: The portion of the term of this patent subsequent to Mar. 11, 1992, has been disclaimed.

[21] Appl. No.: 605,217

[22] Filed: Aug. 15, 1975

Related U.S. Application Data

[63] Continuation-in-part of Ser. No. 518,617, Oct. 29, 1974, Pat. No. 3,989,049.

[51] Int. Cl.³ .......................... A61B 17/12; A61B 1/06
[52] U.S. Cl. ......................................... 128/326; 128/6; 128/303 A; 128/754
[58] Field of Search ............... 128/326, 6, 303 A, 320, 128/4, 306, 2 B, 334 R, 321–324, 754

[56] References Cited

U.S. PATENT DOCUMENTS

| | | | |
|---|---|---|---|
| Re. 25,191 | 6/1962 | Hamilton | 128/326 |
| 2,371,082 | 3/1945 | Vistreich | 128/325 |
| 2,518,994 | 8/1950 | Miller | 128/321 |
| 2,942,604 | 6/1960 | Gravlee, Jr. | 128/303 |
| 3,687,138 | 8/1972 | Jarvik | 128/326 |
| 3,760,810 | 9/1973 | Van Hoorn | 128/326 |
| 3,834,392 | 9/1974 | Lampman et al. | 128/303.13 |
| 3,870,048 | 3/1975 | Yoon | 128/336 |
| 3,882,854 | 5/1975 | Hulka | 128/321 X |
| 3,911,923 | 10/1975 | Yoon | 128/303 A |

Primary Examiner—C. Fred Rosenbaum
Attorney, Agent, or Firm—Finnegan, Henderson, Farabow, Garrett & Dunner

[57] ABSTRACT

A ring applicator device and method for applying an elastic occluding ring to an anatomical tubular structure which comprises an inner cylinder slidably disposed within an outer cylinder, forceps means slidably disposed within said inner cylinder, and means for moving said forceps means into and out of the inner cylinder and for ejecting an elastic ring from the end of said inner cylinder by displacing said outer and inner cylinders relative to each other. The ring applicator device and method is particularly effective in withdrawing a reproductive tubular member inside of the inner cylinder, thereby forming a loop therein, and displacing the inner cylinder relative to the outer cylinder to eject the elastic ring around said loop, in a one-step operation.

55 Claims, 14 Drawing Figures

OCCLUSION RING APPLICATOR

BACKGROUND OF THE INVENTION

The present application is a continuation-in-part application of application Ser. No. 518,617, filed Oct. 29, 1974 and now U.S. Pat. No. 3,989,049.

The present invention relates to an occlusion ring applicator device and method for applying an occluding elastic ring to an anatomical tubular structure. More particularly, the present invention is directed to a ring applicator device, combinations of said device with other instruments, and a technique and method for carrying out tubal ligation of the human female in order to effect temporary or permanent sterilization. The device and method of the present invention can also be effectively utilized to sterilize the human male.

In many areas of the world, the question of population control has become a central issue. Since birth control devices are not always used faithfully or fail to work in some instances, various procedures have been proposed for effecting the sterilization of women as well as men. However, many of these techniques are unpopular because of the resulting complications, the high expense and because of the general unacceptability among the populace of effecting a sterilization which is permanent and cannot be reversed. Nevertheless, sterilization is obviously an effective means for solving various problems of population explosion and of voluntarily limiting the size of the family, where desired, on the part of the parent. Accordingly, research into finding various techniques and instruments has continued both under private and government support.

Tubal ligation has commonly been used to effect sterilization in women. The common practice is to cut and tie the Fallopian tubes in order to prevent sterilization of the egg. More recently, the use of clips for closing the tubes has been suggested. Another recent procedure involves cauterization of the tubes by electrical means. However, each of these procedures involves much discomfort to the patient, and highly skilled personnel are required to complete the operation successfully. Also, in the procedure requiring the use of clips, in some instances the clips have fallen off, thereby rendering the sterilization ineffective. With respect to cauterization by means of electricity, there remains the ever-present dangers of inadvertently burning certain organs of the body and, for example, accidentally rupturing the bowel.

SUMMARY OF THE INVENTION

One of the objects of the present invention is to provide a simplified instrument and method for applying an occlusion ring to an anatomical tubular structure.

Another object of the present invention is to provide a simplified instrument and method for effecting permanent or temporary sterilization of the human female.

A further object of the present invention is to provide a novel technique and instrument for accomplishing tubal ligations which may be employed by physicians with many degrees of skill and without the need of expensive or bulky equipment.

A still further object of the present invention is to provide a portable instrument for mechanically effecting tubal ligation wherein the grasping of an anatomical tubular structure and effecting the release of the elastic ring around a knuckle (bend) formed in the tubular structure to occlude it can be achieved through a single manipulation of a ring applicator device, utilizing only one hand of the operator.

An additional further object of the present invention is to provide a ring applicator device which is physically combined with a laparoscopic system in such a way as to enable the physician operating the device to view the entire ligation operation.

Yet another object of the present invention is to provide a laparoscope which is combined with a ring applicator device in such a manner as to substantially eliminate the possible contamination of the instrument or the physician's hand.

Still another object of the present invention is to provide an instrument which can also be used for the temporary or permanent sterilization of the human male.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and the scope of the invention will become apparent to those skilled in the art from this detailed description.

Pursuant to the present invention, the above-mentioned disadvantages may be eliminated and an improved ligature method and ring applicator device as well as a combination of said device with a laparoscopic system may be obtained by following the teachings of the present invention.

In accordance with the present invention, the sterilization of a reproductive tubular member of the human female or human male may be obtained by the use of elastic rings for effecting a ligature of said reproductive tubular member. Advantageously, the ligature is performed in conjunction with a laparoscope which is an instrument well-known in the medical field for viewing the internal portions of the body. The instrument of the present invention is a ring applicator which is used to quickly and effectively slip a small elastic or rubbery ring around the Fallopian tubes, in the case of the female, in order to temporarily or permanently block the same. Basically, the instrument of the present invention, shown in detail in the attached drawings, includes a grasping means which is used to pull a portion of the Fallopian tube of the female into the device, thereby forming a knuckle or a bend in the Fallopian tube, and slidable tubular or cylindrical means for slipping or pushing the elastic or stretchable ring over the portion of the Fallopian tube held in the device, thereby effecting the ligature. In operation, a natural body entrance is selected near the tubular member to be ligated. In the case of performing the sterilization of the human female, the natural body entrance would be either through the abdominal wall or through the vagina, depending upon the option of the physician. Since the ring applicator could also be used for shortening various ligaments by forming a knuckle therein, the natural body entrance would be selected near the particular tubular member which is desired to be shortened. In the next step of the method, entry is obtained through said natural body entrance by standard medical procedure. For example, when it is desired to ligate the Fallopian tubes, entrance through the abdominal wall may be obtained by making a small incision in the navel area.

When optical viewing means and illuminating means are directly associated with the ring applicator device, only one incision is necessary through the abdominal wall. However, when the light source is an instrument separate from the ring applicator, then the two-hole technique is utilized, that is, one incision is made for the ring applicator device and one incision is made for the optical viewing means and illuminating means. In some instances, if the incision is large enough, a separate optical viewing means and illuminating means may not be necessary. In the next step, the ring applicator and, when desired, the light source, are inserted through said entrance to the location area of said tubular member. Then, a grasping means, e.g., grasping forceps is pushed forward to engage a segment of the Fallopian tube. The grasping means is then retracted into the inner cylinder of the ring applicator device a sufficient distance to form a knuckle or bend in the Fallopian tube and finally, the release of the elastic ring is effected around the knuckle in the Fallopian tube, thereby occluding it. The grasping means can then be released to free the occluded portion of the Fallopian tube from the ring applicator device, leaving a ligatured Fallopian tube. After the ring applicator device has been withdrawn from the body entrance, the entry made through the use of medical procedure is closed where applicable. If desired, the knuckle held by the elastic ring can be cut by the edges of the grasping means in order to effect permanent sterilization. Alternatively, the knuckle can be left as is with the elastic ring holding the Fallopian tube in a crimped position, thereby temporarily or permanently effecting sterilization. Temporary sterilization is contemplated by utilizing an elastic ring which is sufficient to effect a ligature of the Fallopian tube but is not so strong as to cut off the blood supply through the walls of the Fallopian tube. When temporary sterilization is envisioned, the elastic ring can be removed from the Fallopian tube in a subsequent operative procedure.

One of the most advantageous features of the method and device of the present invention is that the grasping of the anatomical tubular structure by the ring applicator device and applying an elastic ring to a knuckle formed in the tubular structure can be accomplished by a single manipulation of the ring applicator device utilizing only one hand of the physician. Thus, after the tubular structure has been grasped by the grasping means, by withdrawing an operating slide by the fore and middle fingers in the rearward direction of the device, not only is the tubular structure drawn into the inner cylinder of the ring applicator, but also, through the continual rearward operation of the operating slide the inner cylinder is drawn within the outer cylinder thereby displacing the elastic ring from the proximal end of the ring applicator device. Thus, by one continuous rearward action of the operating slide, a knuckle is formed in the tubular structure and said tubular structure is ligated with the elastic ring. Simplicity of operation is certainly one of the advantageous features of the present invention.

As stated above, when the applicator device is used in conjunction with a laparoscope, a very small incision may be made when using either the abdominal or vaginal approach because the light associated with the laparoscope facilitates the location of the Fallopian tube. However, when the ring applicator device is used without the aid of the laparoscope, a slightly larger incision is required in order for the physician to locate the Fallopian tubes.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE DRAWINGS

Figure 1:
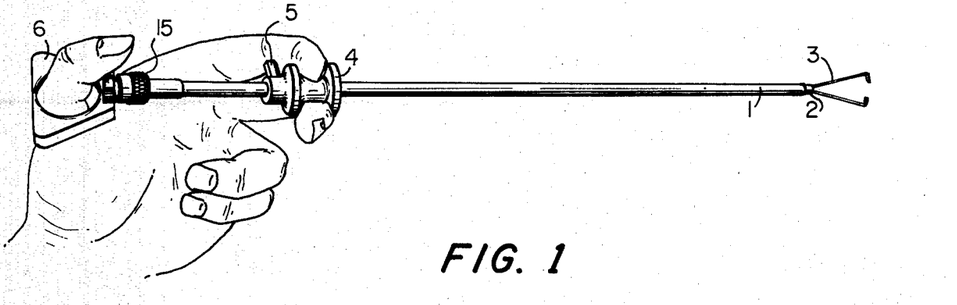
FIG. 1 illustrates the ring applicator device of the present invention and how said ring applicator device is fitted to the physician's hand.

In the following description of the figures, like numbers are used through the various views to indicate like elements. The device of the present invention comprises an inner tube or cylinder 2 disposed within an outer tube or cylinder 1, said inner cylinder being slidably engaged with said outer cylinder. Thus, the inner cylinder 2 can be axially moved relative to the outer cylinder 1. Although the diameter of the inner cylinder can be varied, advantageously, said diameter is in the range of 5 to 7 mm. The inner cylinder is further provided with forceps tongs 3 (grasping means), axially disposed therein. The outer cylinder is provided with an operating slide 4, which through the use of a locking screw 5 is placed in operative engagement with the outer cylinder, the inner cylinder, and the forceps tongs. The distal end of the ring applicator is provided with a thumb ring 6 which is adapted to receive the thumb of the physician.

Figure 2:
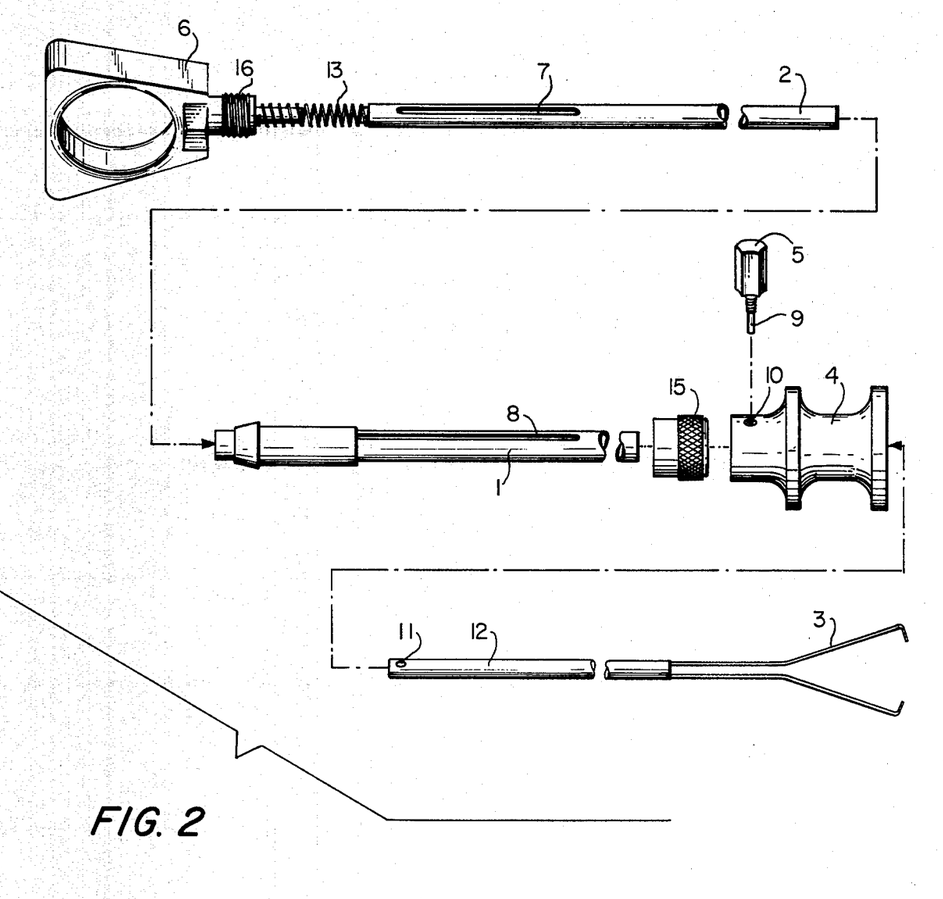
FIG. 2 shows the ring applicator device of FIG. 1 in a disassembled state.
Figure 5:
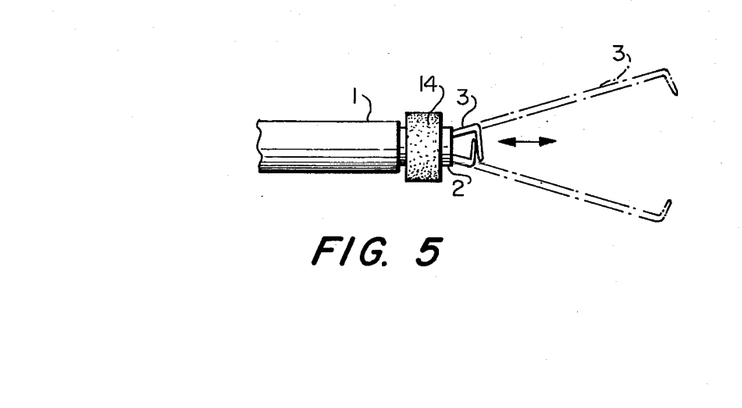
FIG. 5 shows the operation of the grasping means of the ring applicator device.
Figure 6:
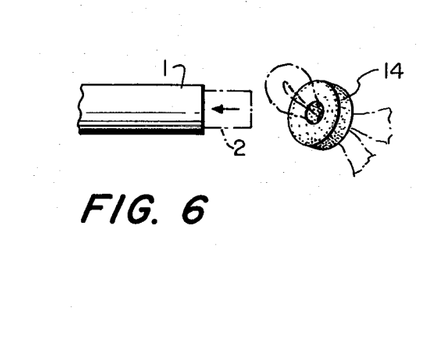
FIG. 6 shows the relative movement of the inner cylinder with respect to the outer cylinder and the knuckle which is formed in the tubular structure.

FIG. 2 shows the ring applicator of FIG. 1 in a disassembled state. The inner cylinder 2 is provided with a slot 7 and the outer cylinder 1 is provided with a slot 8, the slot 8 in the outer cylinder being longer than the slot 7 in the inner cylinder. In its assembled state, the locking screw 5 which contains a stem 9 is screwed into a hole 10 provided in the operating slide 4, the stem 9 extending through the slot 8 in the outer cylinder and the slot 7 in the inner cylinder and into the hole 11 provided in the shaft portion 12 of the forceps tong. Thus, when the operating slide is moved from a position shown in FIG. 1 toward the distal end of the ring applicator device, the stem 9 which is engaged in the hole 11 pulls the forceps tongs into a position inside the proximal end of the ring applicator device as shown in FIG. 5. During this initial operation, since the stem of the locking screw slides through the slots 7 and 8 of the inner and outer cylinders, respectively, said cylinders do not move relative to each other. However, as the operating slide is continually moved toward the distal end of the ring applicator device, the stem 9 will eventually engage the end of the slot 7 of the inner cylinder and thus the inner cylinder will be moved in the rearward direction by the stem 9, thereby compressing the spring 13 and causing the inner cylinder 2 to move inside of the outer cylinder 1 as shown in FIG. 6 which displaces the elastic ring 14 from the proximal end of the ring applicator device. The sliding of the operating slide in the rearward direction will be concluded when the stem 9 engages the end of the slot 8 in the outer cylinder. Thus, the grasping of an anatomical tubular structure and drawing it into a knuckle inside of the ring applicator device and the release of the elastic ring around said knuckle is effected through a single manipulation of the ring applicator device, that is, by merely sliding the operating slide with the fore and middle fingers to the rear of the ring applicator device. When the ring applicator device is assembled, the knurled nut 15 is in engaging relationship with the threaded portion 16 which is adjacent to the thumb ring 6.

Figure 3:
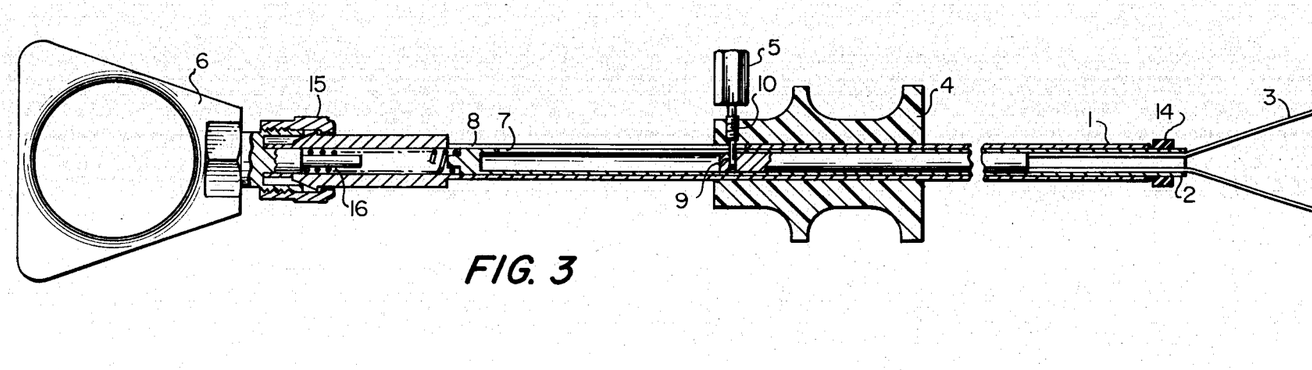
FIG. 3 shows, in cross-section, how the various component parts of the ring applicator device are assembled.

FIG. 3 shows a cutaway profile view of the ring applicator device shown in FIG. 1 wherein the operating slide is in its maximum forward location which extends the forceps tongs fully in the open position. Advantageously, the forceps tongs are spring-loaded so that they spring open when they are displaced from the end of the inner cylinder.

Figure 4:
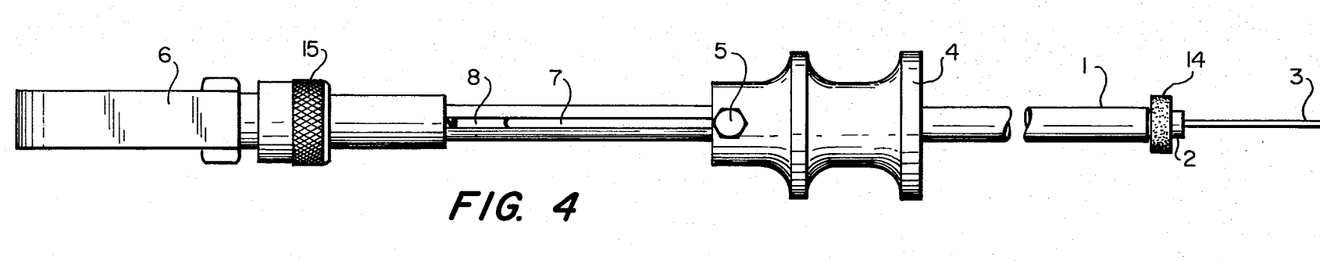
FIG. 4 shows a plan view of the ring applicator device of FIG. 3.

FIG. 4 is a plan view of the ring applicator device of FIG. 3.

Figure 7:
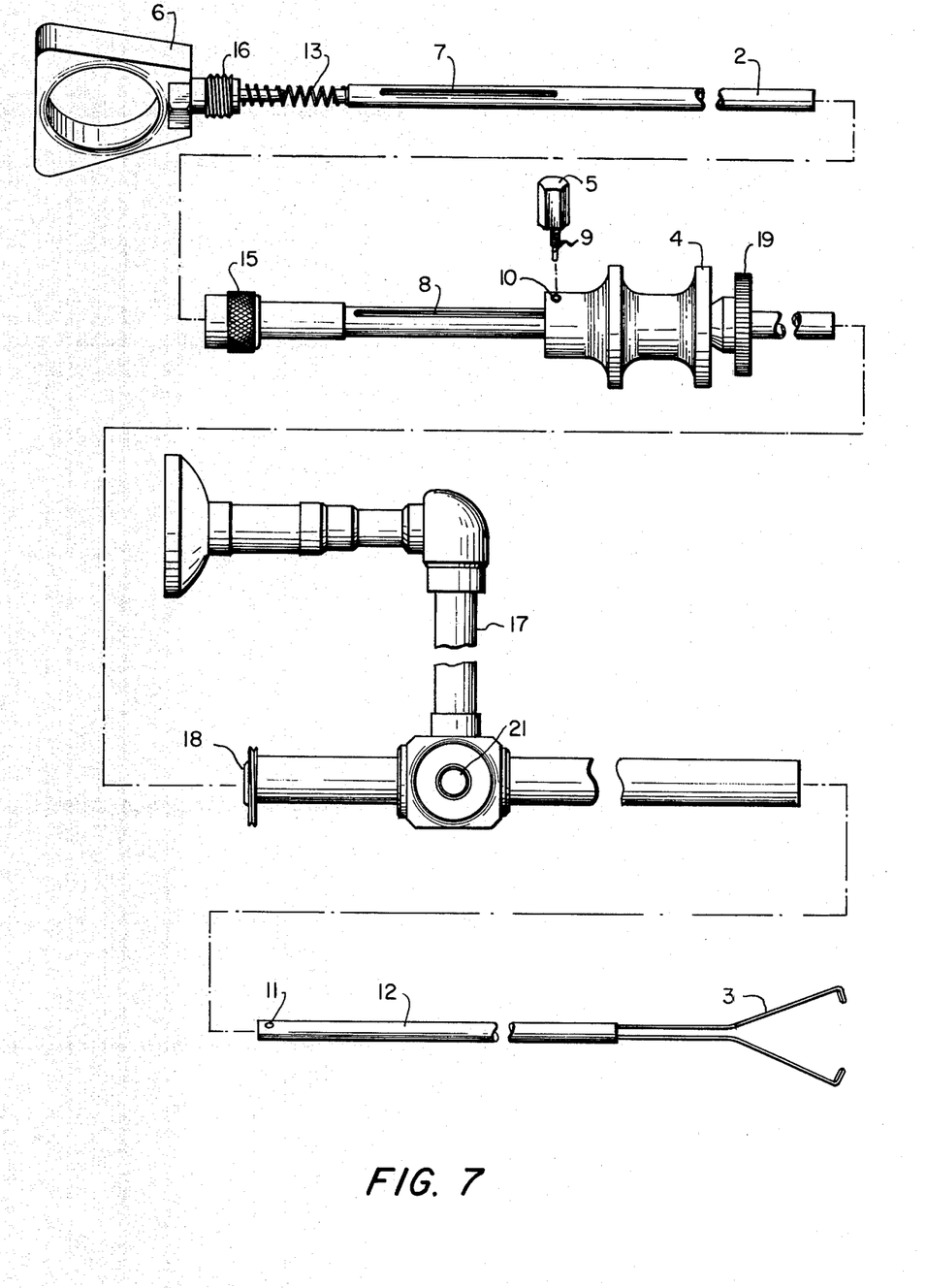
FIG. 7 shows the ring applicator device of the present invention associated with a laparoscope and illustrated in its disassembled form.

FIG. 7 shows the ring applicator of FIG. 1 in combination with a laparoscope. The laparoscope 17 contains a laparoscope operating channel 18 which is adapted to receive the ring applicator device. An applicator lock 19 is utilized to fix the ring applicator device to the laparoscope operating channel. The front end of the laparoscope is represented by lens element 20 in FIG. 10. The light source for the laparoscope is introduced through conduit 21. The light source which is introduced through conduit 21 is transmitted by, for example, fiber optics to the proximal end of the ring applicator device. The fiber optics is represented by elements 22.

Figure 9:
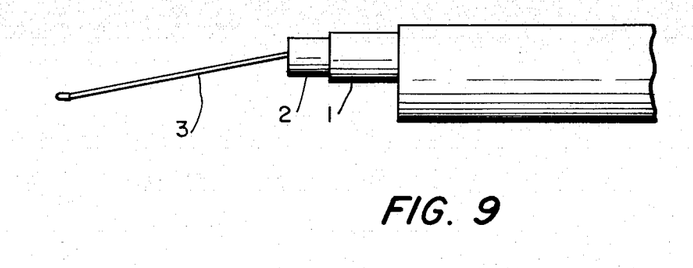
FIGS. 9 and 10 show a side view and a front view of the proximal end of the device of FIGS. 7 and 8.
Figure 10:
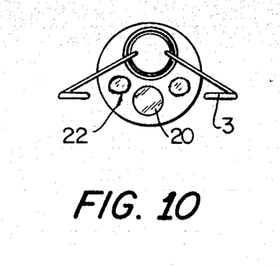

FIGS. 9 and 10 show the relative positioning of the ring applicator device relative to the laparoscope and laparoscope operating channel.

Figure 8:
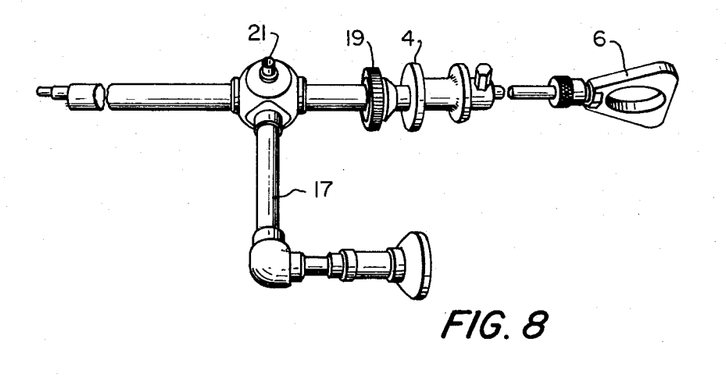
FIG. 8 shows a perspective of the ring applicator device and laparoscope of FIG. 7.
Figure 11:
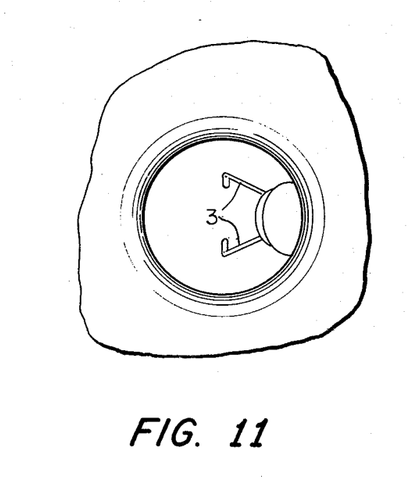
FIG. 11 shows the view which the physician should have of the proximal end of the ring applicator device when looking through the laparoscope.

FIG. 8 shows the laparoscope of FIG. 7 in perspective. As will be noted by referring to FIGS. 7 and 8, the optical viewing means of the laparoscope is offset from its operating channel so that when the operating channel contains the ring applicator, possible contamination of the physician's hand by the face of the physician is avoided. Also, it should be noted that the forceps tongs 3 are also canted from the axial direction of the ring applicator device so that when the physician is looking through the laparoscope it is ensured that the forceps tongs are visible through the laparoscope optics as illustrated in FIG. 11.

As can be readily realized, any optical endoscopic system can be utilized, e.g., laparoscopes, culdoscopes, and hysteroscopes, in conjunction with the ring applicator device of the present invention, either as a separate instrument in connection with the two-hole tubal ligation technique or modified so that it can be physically combined with the ring applicator for implementing the one-hole tubal ligation technique.

Figure 13:
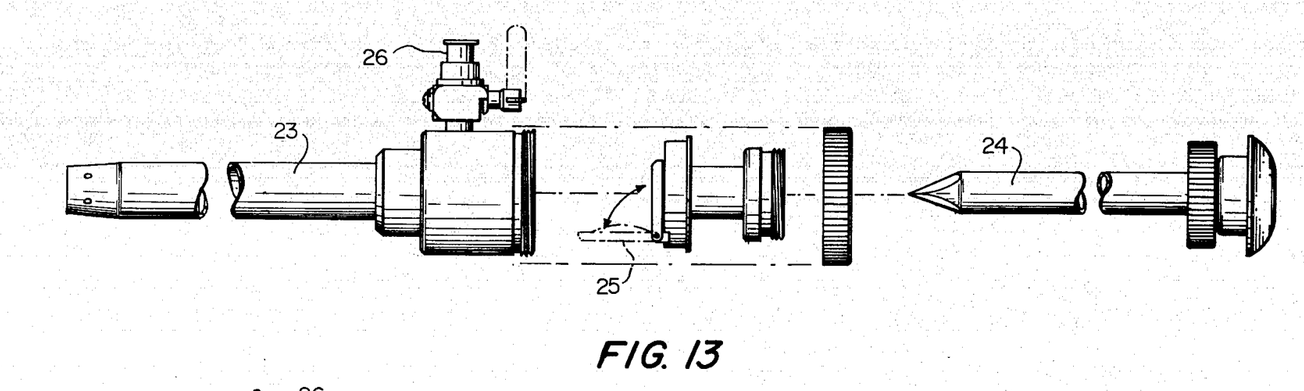
FIG. 13 shows the cannula and trocar of FIG. 12 in a disassembled state.

In the preliminary steps of operation, a ring applicator device is first loaded with an elastic occluding ring. The ring applicator device or a laparoscope containing said device is inserted into a cannula 23 such as that shown in FIG. 13 which has been previously inserted into the patient through an aperture made in the abdominal wall by a trocar 24 which is adapted to be housed by the cannula. One of the particularly advantageous features of the cannula shown in FIG. 13 is the use of a spring-loaded flapper valve 25 which is pushed open when the trocar 24 is inserted into the cannula and automatically springs closed as the trocar is removed from the cannula. The closing of the spring-loaded flapper valve prevents $CO_2$ gas which has been introduced previously into the cannula and the abdomen through inlet valve 26 from leaking from the cannula after the trocar has been removed. The cannula of FIG. 13 represents a substantial improvement over the prior art cannulas which utilize a trumpet valve which must be operated manually in order to open and close the aperture through said cannula.

Figure 12:
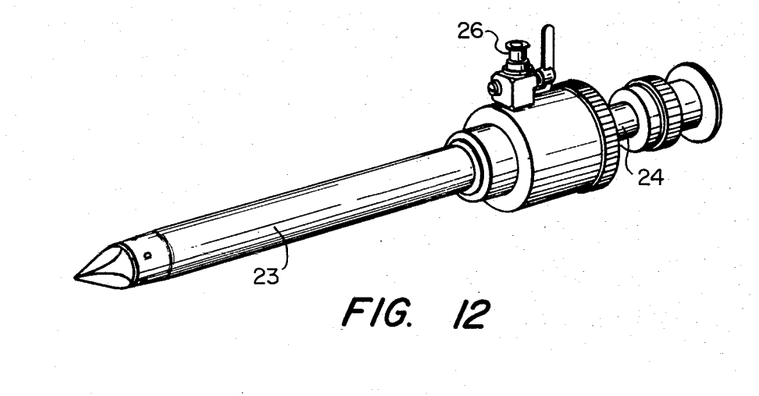
FIG. 12 shows, in a perspective view, a cannula with a trocar associated therewith to facilitate entry of the ring applicator into the body cavity.
Figure 14:
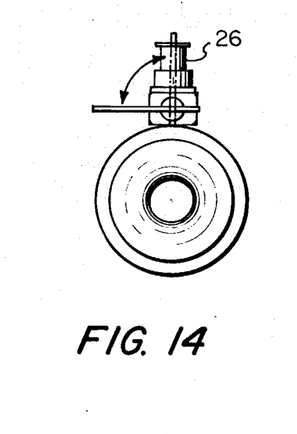
FIG. 14 shows an end view of the cannula and trocar of FIGS. 12 and 13.

FIG. 12 shows in a perspective view the cannula and trocar combined as a single unit, and FIG. 14 shows the cannula of FIG. 13 along the axis of the cannula.

The sterilization operation utilizing the ring applicator device as defined by the present invention renders sterilization so simple that only about 5 to 10 minutes are required to perform the operation and, accordingly, an out-patient procedure may be employed where permitted. This is particularly important in developing countries where hospital facilities are not abundant and may not even be available.

A particular advantage of the present invention is that the blockage of the tubes can be made permanent or temporary, as desired. This particular feature of the invention depends upon the size and the elastic power of the rings employed. If the rings are very small and have a strong elastic power, they will so tightly grip the Fallopian tubes that the blood supply in this part of the tube will be completely blocked, thereby resulting in a sluffing off of the knuckle formed in the tube to effect a permanent sterilization. However, if the elastic bands are of a larger size and/or have a smaller elastic power, it is possible to effect a temporary or reversible sterilization since, although the elastic band will serve to prevent the ovum passage to the uterus, the holding power thereof will not be so strong as to shut off the blood supply through the walls of the Fallopian tubes. In this situation, the knuckle formed in the tubes will remain and will not sluff off. Accordingly, if the woman should desire to return to a normal situation at a later time, it would be possible for the Fallopian tubes to be restored to their natural function by merely removing the elastic rings. Hence, the results of permanent or temporary sterilization are dependent upon the size of the rings used and/or the elastic power thereof.

The rings used for application to the Fallopian tubes are made of government-approved, non-tissue reactive material which has a strong enough elastic power to perform the function described herein. Various rubbery materials may, of course, be used. The preferred material is silicone rubber, for example, the material commercially available under the name "Silastic". Collagen or any other absorbable or nonabsorbable synthetic elastic material which is not harmful to human tissue may be employed, for example, latex rubber or Teflon (tetrafluoroethylene). As pointed out above, the size of the rings may also be varied wherein smaller rings are used for permanent tubal ligation, and larger rings are used in connection with effecting a temporary sterilization. Spring-like metal rings, preferably made of stainless steel, can also be used, as discussed above.

The device of the present invention can be made of medically-approved materials, including many different types of metals, preferably stainless steel, plastics and the like and, hence, is relatively inexpensive because of its simple nature. It can also be made as a disposable instrument, for example, from a synthetic resin such as polyethylene, polypropylene, polycarbonate, polystyrene, polyamide, polyacetate, or acrylic resin. In this embodiment, the wall of the ring applicator can itself act as a laparoscope for transmitting the light from a light source to the internal cavity, and a tube can be disposed around the inner cylinder (which would have a needle-like point) to push an elastic ring over the salpinx portion of the Fallopian tube when it is slid or otherwise moved with respect to said inner cylinder. This embodiment of the invention would be especially attractive where inexpensive instruments are a necessity. Moreover, the ring applicator device of the present invention has a wide range of applicability since it can be used in conjunction with the regular abdominal laparoscopic technique, as discussed above, or in connection with the known vaginal culdascopic procedure. The use of the device eliminates the need for large, bulky equipment which is normally used with the electrical procedures employed in the prior art as well as the complicated carbon dioxide supply system used with other techniques. A very simple and relatively small carbon dioxide sypply system can be used together with the instrument, or a squeeze bulb may be used to provide the necessary gas and to maintain the required gas pressure inside the abdominal cavity while the operation is being performed. The elimination of complicated electrical and gas supply systems makes it possible to save time in setting up for the procedure. In addition, as pointed out above, the operation may be carried out quite quickly, in less than 10 minutes.

It is understood that various specific mechanical embodiments may be employed to perform the various functions described herein. Basically, the invention comprises an instrument for puncturing and entering into the body cavity, grasping the Fallopian tubes, slipping an elastic ring thereover, and optionally cutting the tubes, if desired. The associated equipment represents technical modifications and adds to this basic idea, and a particularly preferred embodiment is the use of the ring applicator of the invention together with a laparoscope or a similar viewing instrument.

In an analogous manner, the method and device of the present invention may be used to effect the sterilization of the human male. In this case, the appropriate incision is made and one or more elastic rings are applied to the vas to effect the ligature thereof and block the passage of the sperm. The elastic or stretchable rings used in this connection must, of course, be small enough to ligate the small diameter of the vas.

It is readily apparent that the device of the present invention can be used to occlude any anatomical tubular structure for any purpose.

Since the single most important feature of the present invention is that the grasping of the reproductive tubular member by the ring applicator device and applying an elastic ring to a knuckle formed in the tubular structure can be accomplished by a single manipulation of the ring applicator device utilizing only one hand of the physician, it is readily apparent that the ring applicator can be modified in many ways to achieve this result. For example, the slot in the inner cylinder can extend to the end of said cylinder so that, in effect, the engagement of the stem 9 with the end of the cylinder and not with the end of the slot, effects the distal movement of the inner cylinder relative to the outer cylinder.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

It is claimed:

1. A ring applicator device for use in applying an elastic occluding ring to an anatomical tubular structure which comprises an inner cylinder and an outer cylinder, said inner cylinder being slidably disposed within said outer cylinder, forceps means slidably disposed within said inner cylinder and operating slide means operatively associated with the forceps means and the inner and outer cylinders for distally displacing the forceps means relative to the inner cylinder and the forceps means and the inner cylinder relative to the outer cylinder as the result of a single continuous movement of said operating slide means toward the distal end of the ring applicator.

2. The ring applicator device of claim 1, wherein connecting means provide communication between the operating slide means and the forceps means independent of the inner and outer cylinders, said forceps means thereby being capable of independent movement in both the proximal and distal directions relative to the inner and outer cylinders.

3. The ring applicator device of claim 2, wherein the inner cylinder is provided with a means for engaging the connecting means independent of the outer cylinder, said inner cylinder thereby being capable of independent movement in the distal direction relative to the outer cylinder.

4. The ring applicator device of claim 3, wherein the forceps means contain a shaft portion and the inner and outer cylinders are provided with first and second operating slots, respectively, said connecting means extending through said first and second operating slots and into engaging relationship with said shaft portion.

5. The ring applicator of claim 4, wherein the first operating slot is shorter than said second operating slot and the means for engaging said connecting means is the distal end of the first operating slot.

6. The ring applicator of claim 4 wherein the first operating slot is shorter than said second operating slot and extends to the distal end of the inner cylinder, and the means for engaging said connecting means is said distal end of the inner cylinder.

7. The ring applicator device of claim 1, wherein a spring means is attached to the distal end portion of the inner cylinder, said spring means being compressed by the movement of the forceps means and the inner cylinder in the distal direction relative to the outer cylinder.

8. The ring applicator device of claim 1, wherein an optical viewing means and an illuminating means are combined with the ring applicator device.

9. The ring applicator devoce of claim 8, wherein the optical viewing means and illuminating means is a laparoscope.

10. The ring applicator of claim 9, wherein the laparoscope is provided with an operating channel, said operating channel receiving the ring applicator device and said optical viewing means being offset from said operating channel and the ring applicator device disposed therein.

11. The ring applicator device of claim 1, wherein said device is made of a metallic material.

12. The ring applicator device of claim 1, wherein said device is made of a plastic material, the walls of said cylinders acting to transmit light from a light source to the abdominal cavity.

13. A ring applicator device for use in applying an elastic occluding ring to an anatomical tubular structure which comprises an inner cylinder provided with a first operating slot and an outer cylinder provided with a second operating slot which is longer than said first operating slot, said inner cylinder being slidably disposed within said outer cylinder, forceps means slidably disposed within said inner cylinder, said forceps means containing a shaft portion which has an engageable end portion, and an operating slide means disposed on said outer cylinder, said operating slide means provided with connecting means which extends from the operating slide, through said first and second operating slots and into engaging relationship with said engageable end portion.

14. The ring applicator device of claim 13, wherein when the operating slide means is in its forward extended position the proximal end portion of the inner cylinder extends beyond the proximal end portion of the outer cylinder and the forceps means extends from the end portion of the inner cylinder.

15. The ring applicator device of claim 14, wherein the front end of the first and second slots are in alignment so that as the operating slide means is drawn toward the distal end of the device, the forceps means is drawn into the inner cylinder and the connecting means engages the rear end portion of the first operating slot which moves the inner cylinder in the distal direction relative to the outer cylinder.

16. The ring applicator device of claim 13, wherein the engageable end portion of said shaft is an aperture and the connecting means is a locking screw which extends from the operating slide means through said first and second operating slots and into screw engagement with said aperture.

17. The ring applicator device of claim 13, wherein a thumb ring is provided at the distal end of the device.

18. The ring applicator device of claim 17, wherein a spring is provided between the thumb ring and the distal end of the inner cylinder.

19. The ring applicator device of claim 13, wherein the forceps means are spring-loaded so that they spring open when they are displaced from the proximal end of the inner cylinder.

20. The ring applicator device of claim 13 wherein the operating slide means is provided with a groove for receiving the fingers of the operator.

21. The ring applicator device of claim 13, wherein an optical viewing means and an illuminating means are combined with the ring applicator device.

22. The ring applicator device of claim 21, wherein the optical viewing means and illuminating means is a laparoscope.

23. The ring applicator device of claim 13, wherein a culdoscope is combined with the ring applicator, said culdoscope and ring applicator being in juxtaposition with respect to each other.

24. The ring applicator device of claim 22, wherein the laparoscope contains an operating channel for receiving the ring applicator device.

25. The ring applicator device of claim 24, wherein the optical viewing means is off-set with respect to the operating channel of the laparoscope.

26. The ring applicator device of claim 13, wherein the forceps means are canted from the axial direction of the ring applicator device.

27. The ring applicator device of claim 13, wherein a handle means is provided at the distal end of the device.

28. A ring applicator device for use in applying an elastic occluding ring to an anatomical tubular structure which comprises a cylinder-type element, the proximal end portion of said cylinder-type element being adapted to receive said elastic occluding ring, forceps means associated with said cylinder-type element and operative to grasp the anatomical tubular structure and draw it inside said cylinder-type element to form a bend therein, a ring pushing means movably and operatively associated with said cylinder-type element for displacing the elastic occluding ring from said cylinder-like element to a position around said bend, thereby forming a closed loop in said anatomical tubular structure and operating slide means operatively associated with the cylinder-like element, the forceps means and the ring pushing means for effecting relative movement therebetween, whereby both the forceps means and the cylinder-like element are distally displaced relative to the ring pushing means as a result of a single continuous movement of said operating slide means in the distal direction and thereafter the forceps means is displaced in the proximal direction to release the occluded anatomical tubular structure from the ring applicator device.

29. The ring applicator of claim 28, wherein the ring pushing means is an additional cylinder-like element within which said cylinder-like element is slidably disposed.

30. In a surgical ligating instrument for tubal ligation within the human and/or animal body by the application of at least one elastic ring to an anatomical tube, the combination which comprises:
 (a) an elongated inner member having a forward end and a rearward end and having a grasping means at its forward end constructed and arranged for grasping the anatomical tube to be ligated,
 (b) tube means adapted to fit slidably over said member (a) with close sliding fit therebetween,
 (c) said tube means (b) having a surface adjacent its forward end over which an elastic ring is adapted to fit in a tensioned condition,
 (d) manually engageable actuating means operatively connected to said member (a) to slide it rearwardly within said tube means (b), (e) means operative upon retraction of said member (a) relative to tube means (b) to actuate said grasping means to grasp the anatomical tube to be ligated and to draw it rearwardly into tube means (b), (f) ejecting means operative upon further retraction of said member (a) concurrently with said tube means (b) to eject said elastic ring from the surface of tube means (b) while said anatomical tube to be ligated extends into said tube means (b), thereby releasing said tensioned ring into a position surrounding said anatomical tube and effecting tubal ligation, and, (g), means for detecting said further retraction of said member (a) comprising a resistance means operatively associated with said manually engageable actuating means (d) for imposing thereon a manually detectable progressively increasing resistance to said further retraction of said member (a) relative to said tube means (b) prior to the ejection of the elastic ring.

31. The instrument defined in claim 30, wherein a stop means is provided in a position to prevent further retraction of said member (a) after said elastic ring (c) has been ejected in response to said further retraction of said member (a).

32. The instrument defined in claim 31, wherein said ejecting means (f) comprises an outer tube within which said tube means (b) is slidably arranged.

33. The instrument defined in claim 32, wherein said resistance means normally positions the forward end of outer tube rearwardly of the forward end of tube means (b).

34. The instrument defined in claim 30, wherein said resistance means includes a mechanical spring.

35. The instrument defined in claim 34, wherein said spring is substantially helical and biases said tube means (b) toward said grasping means, and wherein said further retraction compresses said spring.

36. The instrument defined in claim 35, wherein the forward end of said spring abuts the rearward end of said tube means (b) and wherein a handle is attached to the rearward portion of said outer tube, and wherein said manually engageable actuating means (d) is attached to said inner member (a), and engageable upon tube means (b) whereby said spring may be compressed by relative movement between said handle and said manually engageable actuating means (d).

37. The instrument defined in claim 36, wherein said handle includes a curved hole adapted for operation by insertion of the surgeon's thumb.

38. The instrument defined in claim 36, wherein said handle has a substantially flat rearward surface.

39. In a surgical ligating instrument for tubal ligation within the body by the application of at least one elastic ring, the combination which comprises:

(a) a straight, elongated rod having forceps means at its forward end and having a rearward end spaced from said forward end, (b) a straight, elongated inner tube closely slidably fitted over said rod (a), (c) a straight, elongated outer tube closely slidably fitted over said inner tube (b), (d) yieldable means providing an progressively increasing yielding resistance connecting outer tube (c) to inner tube (b) with the forward end of inner tube (b) projecting forwardly beyond the forward end of outer tube (c), and (e) manually operable means connected to said rod (a) for moving said rod (a) independently of said inner tube (b) without encountering said yielding resistance, said manually operable means (e) also connected to said tube (b) to retract said tube (b) and rod (a) against said yielding resistance after said independent movement of rod (a), but prior to the ejection of said elastic ring.

40. The instrument defined in claim 39, wherein said manually operable means (e) extends outside said outer tube (c) and wherein both said inner tube (b) and said outer tube (c) are provided with openings permitting said independent movement, and wherein said manually operable means includes a connection extending inwardly through said openings.

41. The instrument defined in claim 40, wherein said inner tube opening includes a stop member engageable by said connection to limit independent movement of said rod (a) rearwardly of said inner tube (b).

42. The instrument defined in claim 39, wherein said outer tube includes a stop positioned for limiting rearward movement of said inner tube (b) relative to said outer tube (c).

43. The instrument defined in claim 41, wherein said outer tube includes a stop limiting rearward movement of inner tube (b) relative to outer tube (c), and wherein said outer tube stop is spaced rearwardly of said inner tube stop, whereby in a single rearward movement of said manually operable means (e) said rod (a) moves rearwardly of both tubes (b) and (c), then the rod (a) and inner tube (b) move rearwardly in unison, and then said motion in unison is stopped.

44. The instrument defined in claim 39, including means for disassembling said rod and said tubes each from each other for separate cleaning and sterilization.

45. The instrument defined in claim 40, wherein said openings are slotted openings.

46. The instrument defined in claim 45, wherein said yieldable means (d) interconnecting tube (c) to tube (b), also predetermines the spacing of said slotted openings, and wherein the slotted opening in outer tube (c) extends rearwardly of the slotted opening of inner tube (b), whereby the slotted opening of inner tube (b) provides a stop which is contacted by said connection.

47. The instrument defined in claim 39, wherein said outer tube (c) includes connecting means for connection to an optical viewing device having a viewing bore substantially parallel to said rod (a).

48. The instrument defined in claim 39, wherein said yieldable means is a substantially helical compression spring abutting the rearward portion of said inner tube (b).

49. The instrument defined in claim 39, wherein an elastic occluding ring is stretched and maintained under tension upon the forward end of inner tube (b), and wherein said ring is expelled from inner tube (b) upon movement of inner tube (b) rearwardly into outer tube (c) by contact of said ring with the forward end of outer tube (c).

50. The instrument defined in claim 49, wherein said forward end of inner tube (b) projects forwardly of the front end of outer tube (c) by a distance greater than the thickness of said elastic occluding ring.

51. The instrument defined in claim 40, wherein said connection is threaded to said manually operable means (e).

52. The instrument defined in claim 51, wherein said connection includes a projection which extends into a cavity formed in said rod.

53. The instrument defined in claim 51, wherein said projection has a cylindrical outer surface and said cavity is correspondingly shaped.

54. In a surgical ligating instrument for tubal ligation within the body by the application of at least one elastic ring to an anatomical tube, the combination which comprises:
   (a) a straight, elongated rod having grasping means at its forward end and having a rearward end spaced from said forward end,
   (b) a straight, elongated inner tube closely slidably fitted over said rod (a) and having a surface adjacent its forward end over which an elastic ring is adapted to fit in a tensioned condition,
   (c) a straight, elongated outer tube closely slidably fitted over said inner tube (b),
   (d) manually engagable actuating means operatively connected to said rod (a) to slide it rearwardly within said inner tube (b) and thus actuate such grasping means to grasp the anatomical tube to be ligated and to draw it rearwardly into said inner tube (b),
   (e) means to stop the rearward movement of rod (a) in inner tube (b) when the grasped anatomical tube has been retracted into the forward end of the inner tube (b) and to provide for the further retraction thereafter of rod (a) and inner tube (b) in fixed relationship to each other within outer tube (c),
   (f) spring means at the rearward end of inner tube (b) adapted to impose a manually detectable progressively increasing resistance upon said further retraction of said rod (a) and inner tube (b) relative to said outer tube (c) and prior to the ejection of said elastic ring, and
   (g) ejecting means operative upon said further retraction to eject said elastic ring from the surface of said tube (b) while said anatomical tube to be ligated extends into said tube (b), thereby releasing said tensioned ring into a position surrounding said anatomical tube and effecting tubal ligation.

55. In a surgical ligating instrument for tubal ligation within the body by the application of at least one elastic ring, the combination which comprises:
   (a) a straight, elongated rod having forceps means at its forward end and having a rearward end spaced from said forward end,
   (b) a straight, elongated inner tube closely slidably fitted over said rod (a),
   (c) a straight, elongated outer tube closely slidably fitted over said inner tube (b),
   (d) yieldable means providing a yielding resistance connecting outer tube (c) to inner tube (b) with the forward end of inner tube (b) projecting forwardly beyond the forward end of outer tube (c) and
   (e) manually operable means for movement of said rod (a) relative to said inner tube (b) and said outer tube (c) without encountering said yielding resistance and for movement of said inner tube (b) relative to said outer tube (c), said yieldable means adapted to impose a manually detectable progressively increasing in resistance upon retraction of said inner tube (b) relative to said outer tube (c) and prior to the ejection of said elastic ring.

* * * * *